(12) United States Patent
Vertesy et al.

(10) Patent No.: US 6,599,930 B2
(45) Date of Patent: Jul. 29, 2003

(54) CONIOSETIN AND DERIVATIVES THEREOF, PROCESS FOR THE PREPARATION AND THE USE THEREOF

(75) Inventors: Laszlo Vertesy, Eppstein-Vockenhausen (DE); Martin Knauf, Root (CH); Astrid Markus-Erb, Unterliederbach (DE); Luigi Toti, Hochheim (DE); Marie-Cecile Raynal-Wetzel, Paris (FR); Florence Fassy, Paris (FR)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 10/003,413

(22) Filed: Dec. 6, 2001

(65) Prior Publication Data

US 2002/0137788 A1 Sep. 26, 2002

(30) Foreign Application Priority Data

Dec. 7, 2000  (DE) .......................................... 100 60 810

(51) Int. Cl.$^7$ ...................... A61K 31/42; C07D 207/02; C12P 17/10; C12P 1/02; C12N 1/14
(52) U.S. Cl. ...................... 514/423; 548/539; 435/121; 435/171; 435/254.1
(58) Field of Search .................... 548/539; 514/423; 435/121, 171, 254.1

(56) References Cited

U.S. PATENT DOCUMENTS

| | | | |
|---|---|---|---|
| 3,959,468 A | 5/1976 | Burmeister | 424/122 |
| 5,759,842 A | * 6/1998 | Dombrowski et al. | 435/252.1 |

FOREIGN PATENT DOCUMENTS

| | | | |
|---|---|---|---|
| GB | 2 306 476 A | 5/1997 | |
| WO | WO 00/28064 | 5/2000 | C12P/17/16 |

OTHER PUBLICATIONS

Yuki, et al, 2001, Tetrahedron Letters, 42(13), 2517–2519.*
Rosen, T., et al. "Aromatic Dienoyl Tetramic Acids. Novel Antibacterial Agents with Activity against Anaerobes and Staphylococci," J. Med. Chem. (32):1062–1069 (1989).
Hashidoko, Y. et al. "Structure elucidation of xanthobaccin A, a new Antibiotic produced from Stenotrophomonas sp. strain SB–K88," Tetrahedron Letters, vol. 40:2957–2960 (1999).
Höltzel, A. et al., "Das erste niedermolekulare Antibiotikum aus lebensmitteltechnologisch eingesetsten Milchsäurebakterien: Reutericyclin, eine neue Tetramsäure," Angew.Che., vol. 112(15):2886–2888 (2000).
Li, J. Y. et al., "Cryptocin, a potent tetramic acid antimycotic from the endophytic fungus Cryptosporiopsis cf. quercina," Chemical Abstracts, vol. 132(22):354 (#290935s) (2000).
Li, J. Y. et al., "Cryptocin, a potent tetramic acid antimycotic from the endophytic fungus Cryptosporiopsis cf. quercina," Organic Letters, vol. 2(6):767–770 (2000).
Nowak, A. et al., "Physarorubinic acid, a polyenoyltetramic acid type plasmodila pigment from the slime mold Physarum polycephalum (myxomycetes)," Liebigs Ann./Recueil, 1817–1821 (1997).
Ohta, S. et al., "Ancorinoside A: A novel tetranime acid glycoside from the marine sponge, Ancorina sp. which specifically inhibits blastulation of starfish embryos," Journal of Organic Chemistry, vol. 62:6452–6453 (1997).
Ono, M. et al., "Structure and biosynthesis of aflastatins: Novel inhibitors of aflatoxin production by Aspergillus parasiticus," The Journal of Antibiotics, vol. 51(11):1019–1028 (1998).
Osterhage, C. et al., "Ascosalipyrrolidinone A, an antimicrobial alkaloid, from the obligate marine fungus Ascochyta salicorniae," Journal of Organic Chemistry, vol. 65:6412–6417 (2000).
Remingtons Pharmaceutical Sciences, vol. 17:1418–1431 (1985).
Royles, B.J.L. "Naturally occurring tetramic acids: Structure, isolation, and synthesis," Chemical Reviews, vol. 95:1981–2001 (1995).
Sawa, R. et al., "Harzianic acid, a new antimicrobial antibiotic from a fungus," The Journal of Antibiotics, vol. 47(6):731–732 (1994).
Sasaki, T. et al., "Novel antibiotic PF 1052 and its manufacture with Phoma species," Chemical Abstracts, vol. 118:761 (#211424j) (1993).
Sata, N. et al., "Rubrosides A–H, new bioactive tetramic acid glycosides from the marine sponge Siliquariaspongia japonica," Journal of Organic Chemistry, vol. 64:2331–2339 (1999).
Singh, S. et al., "Equisetin and a novel opposite stereochemical homolog phomasetin, two fungal metabolites as inhibitors of HIV–1 integrase," Tetrahedron Letters, vol. 39:2243–2246 (1998).
Suzuki, S. et al., "Antifungal substances against pathogenic fungi, talaroconvolutins, from Talaromyces convoluts," Chemical Abstracts, vol. 133(2): 285 (#14413p) (2000).
Suzuki, S. et al., "Antifungal substances against pathogenic fungi, talaroconvolutins, from Talaromyces convolutus," Journal of Natural Products, vol. 63:768–772 (2000).
Tanaka, A. et al., "F–10778, a new antifugal antibiotic product by the discomycete Tapesia sp.," Annual Report Sankyo Res. Lab., vol. 49:135–141 (1997).

* cited by examiner

Primary Examiner—Joseph K. McKane
Assistant Examiner—Andrea D. Small
(74) Attorney, Agent, or Firm—Finnegan, Henderson, Farabow, Garrett & Dunner, LLP

(57) ABSTRACT

The present invention relates to novel active substances (coniosetin and coniosetin derivatives) of the formula I

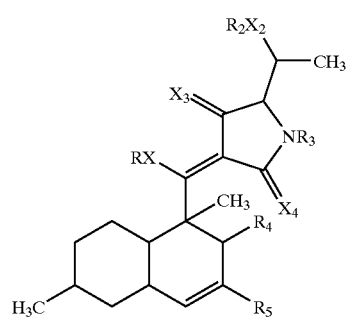

which are produced by the microorganism *Coniochaeta ellipsoidea* Udagawa (DSM 13856) during fermentation, wherein R, $R_2$, $R_3$, $R_4$, $R_5$, X, $X_2$, $X_3$ and $X_4$ have the meanings stated in the specification, to chemical derivatives of coniosetin, to a process for their preparation and to their use as pharmaceuticals.

17 Claims, No Drawings

CONIOSETIN AND DERIVATIVES THEREOF, PROCESS FOR THE PREPARATION AND THE USE THEREOF

The present invention relates to a novel active substance, coniosetin, of the tetramic acid type, which is produced by the microorganism *Coniochaeta ellipsoidea* Udagawa (DSM 13856) during fermentation, to chemical derivatives derived from coniosetin, to a process for the preparation thereof, and to a method for using the novel tetramic acids as pharmaceuticals.

A relatively large number of antibiotics with a tetramic acid basic structure has already been described. Tetramic acid, 2,4-pyrrolidinedione, is the parent compound of various natural substances produced by some microorganisms and marine invertebrates. A description of harzianic acid, an antibiotic with very low activity, was published in 1994 (R. Sawa et al., J. Antibiotics 47:731–732 (1994)). A summary article by B. J. L. Royles described the natural tetramic acid derivatives published up to 1994 (Chem. Rev. 95:1981–2001 (1995)).

Further natural tetramic acids have been described since 1995, but only a few have antibacterial properties. Examples include:

- reutericyclin (A. Höltzel et al., Angew. Chem. 112:2886–2888 (2000)), a compound with weak antibacterial activity;
- rubrosides A–H (N. Sata et al., J. Org. Chem. 64:2331–2339 (1999));
- aflastatins (M. Ono et al., J. Antibiotics 51:1019–1028 (1998));
- F-10778 (A. Tanaka et al., Annu. Rep. Sankyo Res. Lab. 49:135–141 (1997));
- ancorinoside A (S. Ohta et al., J. Org. Chem. 62:6452–6453 (1997));
- physarorubinic acid (A. Nowak et al., Liebigs Ann./Recl. 1817–1821 (1997));
- ascosalipyrrolidinone A (C. Osterhage et al., J. Org. Chem. 65:6412–6417 (2000));
- talaroconvolutins (S. Suzuki et al., J. Nat. Prod. 63:768–772 (2000));
- xanthobaccin A (Y. Hashidoko et al., Tetrahedron Lett. 40:2957–2960 (1999));
- equisetin and phomasetin (S. S. Singh et al., Tetrahedron Lett. 39:2243–2246 (1998)), isomeric inhibitors of HIV-1 integrase;
- cryptocin (J. Y. Li et al., Org. Lett. 2:767–770 (2000)), an antimycotic compound; and
- vancoresmycin (N. V. S. Ramakrishna et al., Int. Patent Publikation No. WO 0028064), an antibiotic.

A large number of antibiotics are employed therapeutically for treating bacterial infectious diseases. The pathogens are, however, becoming increasingly resistant to the pharmaceuticals used, and there is in fact a great threat from so-called multiresistant organisms which not only have become resistant to single groups of antibiotics, such as, for example, β-lactam antibiotics, glycopeptides or macrolides, but also harbor more than one resistance. There are even pathogens which have become resistant to all commercially available antibiotics. Therapy is no longer possible for infectious diseases caused by such organisms. Thus, there is a great need for novel agents which can be employed for resistant organisms. Although many thousands of antibiotics have been described in the literature, most of them are too toxic to be employable as pharmaceuticals.

Surprisingly, it has been found that the strain *Coniochaeta ellipsoidea* Udagawa (DSM 13856) is able to produce at least one novel antibiotic, for example coniosetin, which not only has very good antibacterial activity but is also well-tolerated.

The invention consequently relates to the active substances produced by the strain *Coniochaeta ellipsoidea* Udagawa (DSM 13856) and their physiologically tolerated salts, esters, ethers and obvious chemical equivalents.

The invention accordingly relates to compounds of the formula I:

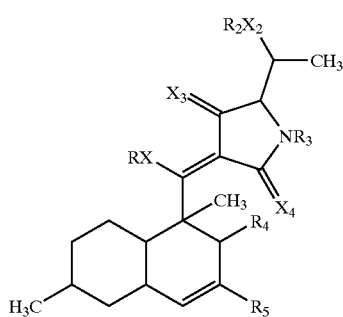

wherein

R, $R_2$ and $R_3$ are, independently of one another:
A. H, or
B. $C_1$–$C_6$-alkyl, $C_2$–$C_6$-alkenyl or $C_2$–$C_6$-alkynyl, in which alkyl, alkenyl and alkynyl are straight-chain or branched and are optionally substituted once or twice by:
B.1 —OH,
B.2 =O,
B.3 —O—$C_1$–$C_6$-alkyl, in which alkyl is straight-chain or branched,
B.4 —O—$C_2$–$C_6$-alkenyl, in which alkenyl is straight-chain or branched,
B.5 —aryl,
B.6 —NH—$C_1$–$C_6$-alkyl, in which alkyl is straight-chain or branched,
B.7 —NH—$C_2$–$C_6$-alkenyl, in which alkenyl is straight-chain or branched,
B.8 —$NH_2$ or
B.9 halogen,
in which substituents B.1 to B.9 may be further substituted by —CN, amide or oxime functions, $R_4$ is $C_1$–$C_6$-alkyl, in which alkyl can be straight-chain or branched and is optionally substituted once or twice as described under B.1 to B.9, or $C_2$–$C_6$-alkenyl, in which alkenyl can be straight-chain or branched, and $R_5$ is H or methyl, and X, $X_2$, $X_3$ and $X_4$ are, independently of one another, O, NH, N—$C_1$–$C_6$-alkyl,
N—$C_2$–$C_6$-alkenyl, N—$C_2$–$C_6$-alkynyl, N-acyl, N-aryl, N—O—R or S.

The invention further relates to stereoisomeric forms of the compound of the formula I and/or mixtures of these forms in any ratio, and/or physiologically tolerated salts of the compound of the formula I.

The invention relates not only to compounds of the formula I (coniosetin and coniosetin derivatives) but also to obvious chemical equivalents as defined below.

In formula I, $C_1$–$C_6$-alkyl is a straight-chain or branched alkyl having 1 to 6 carbon atoms, preferably having 1 to 4 carbon atoms, such as methyl, ethyl, i-propyl, tert-butyl and hexyl, $C_2$–$C_6$-alkenyl is a straight-chain or branched alkenyl having 2 to 6 carbon atoms, which is saturated once, twice or three times, such as, for example, allyl, crotyl, 1-propenyl, penta-1,3-dienyl and pentenyl, and $C_2$–$C_6$-alkynyl is a straight-chain or branched alkynyl having 2 to 6 carbon atoms, which is unsaturated once or twice, such as, for example, propynyl, butynyl and pentynyl.

Aryl can be, for example, phenyl, benzyl or 1- or 2-naphthyl, which may also be substituted, for example, by halogen such as chlorine, bromine, fluorine, by alkyl having 1–4 carbon atoms, such as methyl, by hydroxyl, by alkoxy having 1–4 carbon atoms, such as methoxy and/or by trifluoromethyl.

Acyl can be aliphatic or aromatic acyl radicals. Aliphatic acyl has 1–7, generally 1–4, carbon atoms, such as, for example, formyl, acetyl, propionyl, butyryl, hexanoyl, acryloyl, crotonoyl, propioloyl, which may also be further substituted, for example, by halogen, such as chlorine, bromine, fluorine, by amino, and/or by alkylamino having 1–4 carbon atoms, preferably methyl- or ethylamino groups. Aromatic acyl can be, for example, benzoyl or naphthoyl, which may be further substituted, for example, by halogen, such as chlorine, bromine, fluorine, by alkyl having 1–4 carbon atoms, such as methyl, by hydroxyl, by amino groups such as, for example, ethylamino, or by alkoxy groups having 1–7, generally 1–4, carbon atoms, such as methoxy.

In one embodiment of the invention, compounds of the formula I are those wherein:

$R_3$ is H, $R_4$ is penta-1,3-dienyl, $R_5$ is $CH_3$, $R_2X_2$ is OH, $X_3$, $X_4$ is =O, and RX is OH, and the physiologically tolerated salts thereof.

In yet another embodiment of the invention, compounds of the formula I are those in which $R_3$ is H and $R_4$ is penta-1,3-dienyl.

The invention further relates to a compound of the formula II

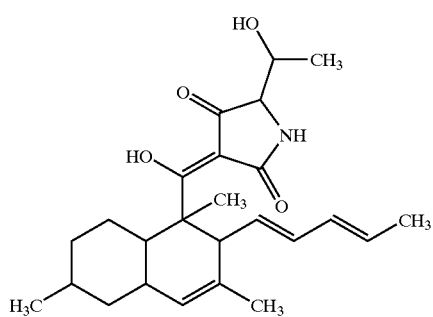

(coniosetin: molecular formula: $C_{25}H_{35}NO_4$; MW 413.56) and the physiologically tolerated salts thereof.

Chirality centers in the compounds of the formula I or II may, unless indicated otherwise, be in the R or in the S configuration. The invention relates both to the optically pure compounds and to mixtures of stereoisomers, such as mixtures of enantiomers and mixtures of diastereomers, in any ratio.

Preferred novel compounds of the formula I are those compounds in which the configuration corresponds to the substituted hydrogenated naphthyl structure of the formula III:

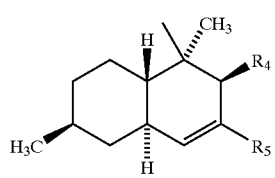

The invention therefore further relates to a compound of the formula IIIA:

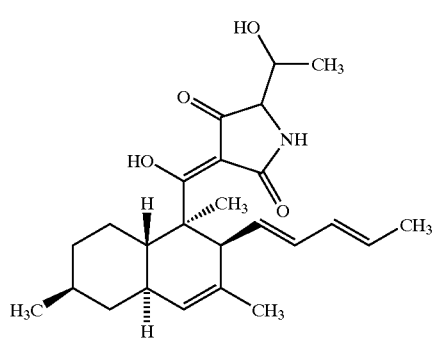

and the physiologically tolerated salts thereof.

The invention additionally relates to a compound of the molecular formula: $C_{25}H_{35}NO_4$ (coniosetin) obtainable by fermentation of *Coniochaeta ellipsoidea* Udagawa (DSM 13856) or one of its variants and/or mutants until the compound coniosetin accumulates in the culture broth and subsequent isolation of the compound, and the pharmacologically acceptable salts thereof.

The invention further relates to chemical derivatives derived from a compound of the molecular formula $C_{25}H_{35}NO_4$ (coniosetin), obtainable by fermentation of *Coniochaeta ellipsoidea* Udagawa (DSM 13856) or one of its variants and/or mutants until the compound coniosetin accumulates in the culture broth, isolation of the compound, and subsequent conversion into chemical derivatives, and the pharmacologically acceptable salts thereof.

The antibiotic coniosetin differs structurally from substances disclosed in the literature. Although structurally related tetramic acid derivatives have been described (see a selection of literature references above), they all differ from the novel compounds either through polarity, through chemical structure, through antimicrobial activity, or through other physical properties.

The invention further relates to a process for preparing the compound of the formula I, which comprises cultivating the microorganism *Coniochaeta ellipsoidea* Udagawa (DSM 13856) or one of its variants or mutants in an aqueous nutrient medium, isolating and purifying a compound of the formula I and, where appropriate, converting it into its pharmacologically acceptable salts.

The strain *Coniochaeta ellipsoidea* Udagawa (DSM 13856) produces coniosetin and byproducts on glucose-, starch-, oatmeal- or glycerol-containing nutrient solutions. An isolate of *Coniochaeta ellipsoidea* Udagawa has been deposited at the Deutschen Sammlung von Mikroorganismen and Zellkulturen GmbH (DSM), Mascheroder Weg 1B, 38124 Braunschweig, Germany, in accordance with the rules of the Budapest Treaty on Nov. 17, 2000, under number DSM 13856.

The fungus Coniochaeta has a white substrate mycelium and very little aerial mycelium. In culture, it forms no fruiting bodies characteristic of Coniochaeta.

Said process comprises the cultivation of *Coniochaeta ellipsoidea* Udagawa (DSM 13856), its mutants and/or variants under aerobic conditions in a culture medium containing carbon and nitrogen sources, inorganic salts and, where appropriate, trace elements.

The cultivation is preferably carried out at a temperature between 20 and 35° C. and at a pH between 3 and 10.

The invention additionally relates to a process for preparing a compound of the formula I which comprises reacting the compound coniosetin with a reagent.

For example, an activated acid can be reacted with hydroxyl groups or the nitrogen of coniosetin. Activated acids are, for example, acid chlorides or other acid derivatives as have been described, for example, by Jerry March in the monograph Advanced Organic Chemistry, John Wiley & Sons, 4$^{th}$ Edition, 1992. In order to carry out reactions selectively, it may be advantageous to introduce suitable protective groups before the reaction, in a manner known to one of ordinary skill in the art. The protective groups are eliminated after the reaction and subsequently the reaction product is purified.

In place of the strain DSM 13856, it is also possible to employ its mutants and variants as long as they produce the novel compounds. A mutant refers to a microorganism in which some gene on the genome is modified, leaving the gene or genes responsible for the organism's ability to produce the compounds of formula (I) in recoverable amounts functional and heritable. Such mutants can be generated in a manner known in the art. It may be by physical means, for example irradiation, such as with ultraviolet or X-rays, or with chemical mutagens such as ethyl methanesulfonate (EMS); 2-hydroxy-4-methoxybenzophenone (MOB) or N-methyl-N'-nitro-N-nitrosoguanidine (MNNG) or as described by Brock et al. in "Biology of Microorganisms," Prentice Hall, pages 238–247 (1984). A variant refers to a phenotype of the microorganism. Microorganisms have the ability to adapt to environmental changes. This adaptive capacity is the reason for the observed physiological flexibility. In phenotypic adaptation, all cells of a population are involved. This type of change is not genetically conditioned. It is a modification that under altered conditions is reversible (H. Stolp, Microbial ecology: organisms, habitats, activities. Cambridge University Press, Cambridge, GB, page 180, 1988).

Screening for mutants and variants which produce the novel antibiotic can take place by determining the biological activity of the active substance accumulated in the culture broth, for example, by determining the antibiotic effect, or by detecting compounds that are known to be active in the culture broth by, e.g., HPLC or LC-MS methods.

Suitable and preferred carbon sources for the fermentation are assimilable carbohydrates and sugar alcohols, such as, for example, glucose, lactose, sucrose or D-mannitol, and carbohydrate-containing natural products such as malt extract or yeast extract. Suitable nitrogen-containing nutrients are: amino acids, peptides and proteins and their degradation products, such as casein, peptones or tryptones, also meat extracts, yeast extracts, ground seeds, for example of corn, wheat, beans, soybean or the cotton plant, distillation residues from the production of alcohol, meat meals or yeast extracts, ammonium salts and nitrates, but in particular peptides obtained synthetically or biosynthetically. Inorganic salts which the nutrient solution may contain are, for example, chlorides, carbonates, sulfates or phosphates of the alkali metals or alkaline earth metals, iron, zinc, cobalt and manganese.

Production of the novel coniosetins takes place particularly well, for example, in a nutrient solution which contains about 0.05 to 5%, generally 1 to 2%, of malt extract, about 0.05 to 3%, generally 0.05 to 1%, of yeast extract, 0.2 to 5%, generally 0.5 to 2%, of glucose, and 0.5 to 3%, generally 1.5% to 3%, of oatmeal. The percentage data are in each case based on the weight of the complete nutrient solution.

In this nutrient solution, *Coniochaeta ellipsoidea* Udagawa (DSM 13856) produces a mixture of coniosetins. The content in terms of quantity of one or more of the novel coniosetins may vary depending on the composition of the nutrient solution. In addition, it is possible to control the synthesis of individual coniosetins through the composition of the media, so that the microorganism may not produce one coniosetin or may produce it in an amount below the detection limit.

The microorganism is cultivated aerobically, i.e., for example, submerged with shaking or stirring in shaken flasks or fermenters or on a solid medium, where appropriate with introduction of air or oxygen. It can be carried out in a temperature range from about 15 to 35° C., generally at about 20 to 30° C., more specifically at 25 to 30° C. The pH range should be between 4 and 10, generally between 6.5 and 7.5. The microorganism is generally cultivated under these conditions over a period of from 48 to 720 hours, more specifically 72 to 720 hours. Cultivation advantageously takes place in a plurality of stages, i.e., initially one or more precultures are prepared in a liquid nutrient medium and are then transferred into the actual production medium, the main culture, for example in a ratio 1:10 to 1:100 by volume. The preculture is obtained, for example, by transferring the mycelium into a nutrient solution and allowing it to grow for about 20 to 120 hours, preferably 48 to 72 hours. The mycelium can be obtained, for example, by allowing the strain to grow for about 1 to 40 days, preferably 21 to 35 days, on a solid or liquid nutrient medium, for example yeast-malt agar, oatmeal agar or potato-dextrose agar.

The progress of the fermentation and the production of the novel antibiotics can be followed by methods known to a person skilled in the art, such as, for example, by determining the biological activity in bioassays, or by chromatographic methods such as thin-layer chromatography (TLC) or high-performance liquid chromatography (HPLC).

The fungus *Coniochaeta ellipsoidea* Udagawa (DSM 13856) is able to produce the compound coniosetin by surface or unstirred culture on solid nutrient media. Solid nutrient media are prepared by adding, for example, agar or gelatin to aqueous nutrient media. It is also possible to obtain coniosetin by fermentation of the fungus *Coniochaeta ellipsoidea* Udagawa in the submerged process, i.e., in aqueous suspension. The antibiotic coniosetin may occur both in the mycelium and in the culture filtrate, and the major quantity is usually found in the biomass. It is therefore expedient to subject the fermentation solution to filtration or centrifugation. The filtrate is extracted with an adsorption resin as solid phase. The mycelium, but also the surface culture, is expediently extracted with methanol or 2-propanol, but it is also possible to use other solvents.

The extractions can be carried out in a wide pH range, but it is expedient to operate in a neutral or weakly acidic medium, preferably between pH 3 and pH 7. The extracts can be concentrated and dried for example in vacuo.

One method for isolating the antibiotic of the invention is solution partition in a manner known in the art.

Another method for purification is chromatography on adsorption resins such as on Diaion® HP-20 (Mitsubishi Casei Corp., Tokyo), on Amberlite® XAD 7 (Rohm and Haas, USA), on Amberchrom® CG, (Toso Haas, Philadelphia, USA) or on similar materials. Numerous reverse-phase supports are also suitable, for example $RP_8$ and $RP_{18}$, as have become generally known, for example, within the framework of high-pressure liquid chromatography (HPLC).

Another possibility for purifying the antibiotic of the invention is to use so-called normal phase chromatography supports such as silica gel or $Al_2O_3$ or others in a manner known in the art.

An alternative isolation process is to use molecular sieves such as Fractogel® TSK HW-40, Sephadex® G-25 and others, in a manner known in the art. It is also possible to obtain the coniosetin by crystallization from concentrated material. Suitable for this purpose are, for example, organic solvents and mixtures thereof, anhydrous or with added water. An additional process for isolation and purification of the antibiotics of the invention is to use anion exchangers, preferably in the pH range from 4 to 10, and cation exchangers, preferably in the pH range from 2 to 5. It is particularly suitable for this purpose to use buffer solutions to which proportions of organic solvents have been added.

Coniosetin, said chemical derivatives thereof and the obvious chemical equivalents thereof can be converted by methods known to the skilled worker and to the corresponding pharmacologically acceptable salts.

Obvious chemical equivalents of the compounds of the invention are compounds which show a slight chemical difference, i.e., have the same activity or are converted under mild conditions into the compounds of the invention. Said equivalents include, for example, esters, azomethines (Schiff's bases), ketals, oximes, hydrogenation products, reduction products, complexes or adducts of the or with the compounds of the invention.

Pharmacologically acceptable salts of the compounds of the invention mean both inorganic and organic salts as described in Remington's Pharmaceutical Sciences (17th edition, page 1418 (1985)). Suitable salts are, in particular, alkali metal, ammonium and alkaline earth metal salts, salts with physiologically tolerated amines and salts with inorganic or organic acids such as, for example, HCl, HBr, $H_2SO_4$, maleic acid, fumaric acid.

Surprisingly, it has been found that the compounds of the invention show strong antibacterial effects and are therefore suitable for the therapy of diseases caused by bacterial infections. Table 1 summarizes the minimum inhibitory concentrations (MIC) of coniosetin by way of example.

TABLE 1

In vitro activity (MIC values (µg/ml)) of coniosetin on Gram-positive bacteria in the serial dilution test.

|  | Resistant to | After 18 h | 24 h | 48 h |
| --- | --- | --- | --- | --- |
| Staphylococcus aureus | ery S | 0.3 | 0.3 | 0.6 |
| S. aureus | oxa S ery R | 0.3 | 0.3 | 0.3 |
| S. aureus | oxa R ery R | 0.3 | 0.3 | 0.3 |
| S. aureus | oxa S ery R | 0.6 | 0.6 | 0.6 |
| S. epidermidis | oxa S ery R | 0.3 | 0.3 | 0.3 |
| S. aureus | oxaR eryR tetR | 0.3 | 0.3 | 0.3 |
| S. aureus | oflR oxaR eryR tetR | 0.6 | 0.6 | 0.6 |
| S. epidermidis | oxa R ery R | 0.6 | 1.2 | 1.2 |
| S. pyogenes | ery S | 0.6 | 1.2 | 1.2 |
| Enterococcus faecalis | ery S | 2.5 | 2.5 | 2.5 |
| Enterococcus faecalis | ery R | 2.5 | 2.5 | 2.5 |
| Enterococcus faecium | teiR vanR eryR tetR | 1.2 | 1.2 | 2.5 |
| Streptococcus gr. G | ery S | 1.2 | 1.2 | 1.2 |
| S. mitis | ery S | 1.2 | 2.5 | 2.5 |
| S. pyogenes | ery R | 1.2 | 1.2 | 1.2 |
| S. agalactiae | ery R | 2.5 | 2.5 | 2.5 |
| Streptococcus gr. G | ery R | 0.6 | 0.6 | 0.6 |

TABLE 1-continued

In vitro activity (MIC values (µg/ml)) of coniosetin on Gram-positive bacteria in the serial dilution test.

|  | Resistant to | After 18 h | 24 h | 48 h |
| --- | --- | --- | --- | --- |
| S. sanguis | ery R | 1.2 | 1.2 | 2.5 |
| S. mitis | ery R | 2.5 | 2.5 | 2.5 |
| S. pneumoniae | ery S | 0.6 | 0.6 | 0.6 |
| S. pneumoniae | ery S pen R | 0.6 | 1.2 | 1.2 |
| S. pneumoniae | ery R | 0.6 | 0.6 | 0.6 |
| S. pneumoniae | ery R pen R | 0.6 | 0.6 | 0.6 |
| S. pneumoniae | ery R pen R | 0.6 | 0.6 | 0.6 |
| S. pneumoniae | ery R | 0.6 | 0.6 | 0.6 |
| S. pneumoniae | ery R | 0.6 | 0.6 | 1.2 |
| Escherichia coli |  | >40 |  |  |

S = sensitive, R = resistant, ery = erythromycin, ofl = ofloxacin, oxa = oxacillin, pen = penicillin, tei = teicoplanin, van = vancomycin, tet = tetracycline.

It is particularly noteworthy that the compound of the invention shows absolutely no cross-resistance with conventional antibiotics such as the β-lactams (penicillins, cephalosporins), aminoglycosides (streptomycin), macrolides (erythromycin), quinolones (ciprofloxacin), sulfonamides or glycopeptides (vancomycin) and others.

Additionally, it should be emphasized that there is an inhibitory effect—although weaker—on yeasts such as, for example, *Candida albicans* and on fungi such as *Aspergillus niger*, which may cause persistent and even life-threatening infectious diseases (Example 8). Therefore, coniosetin is suitable for the therapy of such diseases.

Coniosetin is well-tolerated at the effective concentration and at higher concentrations.

The present invention accordingly also relates to the use of the compounds of the invention as pharmaceuticals, and to the use of the relevant compounds for producing pharmaceuticals for the treatment and/or for the prophylaxis of bacterial infections and mycoses.

The present invention further relates to pharmaceuticals with a content of the compound of the invention.

Said pharmaceutical is produced by mixing at least one compound of the formula I with a physiological excipient and/or carrier and converting into a suitable dosage form.

The pharmaceuticals of the invention may be administered enterally, orally, parenterally (intramuscularly or intravenously), rectally or locally (topically). They can be administered in the form of solutions, powders, tablets, capsules (including microcapsules), ointments (creams or gel) or suppositories. Suitable excipients for such formulations are the pharmaceutically customary liquid or solid fillers and extenders, solvents, emulsifiers, lubricants, flavorings, colorings and/or buffer substances. The dosage expediently administered is 0.1–1000, preferably 0.2–100, mg/kg of bodyweight. They are expediently administered in dosage units which contain at least the effective daily amount of the compounds of the invention, e.g. 30–3000, generally 50–1000, mg.

The following examples are intended to explain the invention in more detail without restricting the scope of the invention in any way.

EXAMPLE 1

Preparation of a Glycerol Culture of *Coniochaeta ellipsoidea* (DSM 13856)

30 ml of nutrient solution (malt extract 2.0%, yeast extract 0.2%, glucose 1.0%, $(NH_4)_2HPO_4$ 0.05%, pH 6.0) in a sterile 100 ml Erlenmeyer flask were inoculated with the strain *Coniochaeta ellipsoidea* Udagawa (DSM 13856) and incubated on a rotating shaker at 25° C. and 140 rpm for 6 days. 1.5 ml of this culture were then diluted with 2.5 ml of 80% strength glycerol and stored at −135° C.

EXAMPLE 2

Preparation of a Preculture of *Coniochaeta ellipsoidea* Udagawa (DSM 13856) in an Erlenmeyer Flask 100 ml of nutrient solution (malt extract 2.0%, yeast extract 0.2%, glucose 1.0% $(NH_4)_2HPO_4$ 0.05%, pH 6.0) in a sterile 300 ml Erlenmeyer flask were inoculated with the strain *Coniochaeta ellipsoidea* Udagawa (DSM 13856) and incubated on a rotating shaker at 25° C. and 140 rpm for 4 days. 2 ml of this preculture were then inoculated to prepare the main cultures.

EXAMPLE 3

Preparation of a Main Culture of *Coniochaeta ellipsoidea* Udagawa (DSM 13856) on Solid Medium Plates 200 ml of the nutrient solution (20 g/l malt extract, 20 g/l oatmeal, 2% agar and pH 7.0 were poured into 30 sterile 25×25 cm plates. These plates were inoculated with 2 ml of a preculture and incubated at 25° C. The maximum production of one or more coniosetin compounds of the invention was reached after about 676 hours.

EXAMPLE 4

Isolation of the Antibiotic Coniosetin

Thirty agar plates, each 25×25 cm in size, obtained as in Example 3, were freeze-dried and extracted with 2.5 liters of methanol. The clear liquid phase was concentrated to 100 ml in vacuo, diluted with water and loaded onto a column with a capacity of 580 ml packed with the adsorption resin MCI Gel® CHP20P. Column dimensions: width×height: 5 cm×30 cm. A solvent gradient from 5% acetonitrile in water to 90% acetonitrile was used for elution, and the column outflow (40 ml/minute) was collected in fractions each of 120 ml. The coniosetin-containing fractions, which were checked by HPLC analyses, were collected and concentrated in vacuo and freeze dried (0.3 g).

EXAMPLE 5

High-pressure Liquid Chromatography (HPLC) of Coniosetin

| | |
|---|---|
| Column: | Superspher 100 RP-18e ®, 250-4, with precolumn, |
| mobile phase: | 75% acetonitrile in 0.1% phosphoric acid, |
| flow rate: | 1 ml per minute, |
| detection by UV absorption at 210 nm. | |

The retention time found for coniosetin was 13.6 min.

EXAMPLE 6

Final Purification of Coniosetin

The enriched antibiotic coniosetin (0.3 g) obtained in Example 4 was fractionated on a LiChrospher® 100 RP-18e HPLC column (width×height=2.5 cm×25 cm) in a gradient process with 75% to 100% acetonitrile in 0.05% acetic acid. Flow rate: 30 ml/min. Fraction size: 60 ml. The fractions investigated by analytical HPLC (see Example 5) were combined according to their coniosetin content, concentrated in vacuo and freeze dried. They afforded 170 mg of coniosetin with a purity of 98%.

EXAMPLE 7

Coniosetin Characterization by Mass Spectrometry

Determination of the molecular peak:

The examined molecule was assigned a mass of 413 on the basis of the following findings: $ESI^+$ spectrum and $FAB^+$ spectra showed peaks at 414 amu $(M+H)^+$. The $ESI^-$ spectrum showed inter alia a peak at 412 amu $(M-H)^-$.

High resolution of the quasi molecular ion:

Under FAB conditions with a nitrobenzyl alcohol matrix, a peak was observed at 414.2645 amu, inter alia. The accuracy of mass in the measurement was about 5 ppm. The measurement agreed well with the elemental composition calculated for $C_{25}H_{36}NO_4 = 414.2644$ amu. Nine double-bond equivalents ware present with this elemental composition.

MS/MS experiments with an ion trap mass spectrometer lead to the following fragmentations in the $ESI^+$ mode:

414 amu to 396 amu ($-H_2O$), 386 amu ($-CO$), 370 amu ($-C_2H_4O$), 346 amu ($-C_5H_8$), 278 amu, 271 amu, 245 amu, 215 amu, 196 amu and other fragments of low intensity. 396 amu to 378 amu ($-H_2O$), 352 amu ($-C_2H_4O$), 253 amu, 241 amu, 227 amu 386 amu to 368 amu ($-H_2O$), 243 amu.

The physicochemical and spectroscopic properties of the antibiotic of the invention can be summarized as follows:
Coniosetin Appearance: colorless to pale yellow substance which is soluble in organic solvents of medium polarity and above but is of low solubility in water. Stable in neutral and weakly acidic media but unstable in strongly acidic and strongly alkaline solution.

| | |
|---|---|
| Molecular formula: | $C_{25}H_{35}NO_4$ |
| Molecular weight: | 413.56 |
| $^1H$ and $^{13}C$ NMR: | see Tables 2 and 3 |
| UV maxima: | 233 nm, 288 nm |

TABLE 2

$^1H$ and $^{13}C$ chemical shifts of coniosetin in DMSO-$d_6$ and methanol-$d_4$ at 300 K.

| | DMSO-$d_6$ | | Methanol-d4 | |
|---|---|---|---|---|
| Position | $^{13}C$ δ (ppm) | $^1H$ δ (ppm) | $^{13}C$ δ (ppm) | $^1H$ δ (ppm) |
| 1 | 48.94 | — | 51.18 | — |
| 1-Me | 13.34 | 1.33 s | 14.31 | 1.42 s, br |
| 2 | 48.45 | 3.19 | 50.59 | 3.28 br |
| 3 | 130.99 | — | 133.15 | — |
| 3-Me | 22.04 | 1.53 t | 22.67 | 1.58 t |
| 4 | 125.88 | 5.19 s, br | 127.31 | 5.20 s |
| 5 | 38.61 | 1.80 | 40.68 | 1.86 m |
| 6 | 42.06 | 1.78, 0.82 | 44.10 | 1.83 d, br, 0.87 m |
| 7 | 32.90 | 1.49 | 35.00 | 1.52 m, br |
| 7-Me | 22.40 | 0.89 d | 23.07 | 0.94 d |

TABLE 2-continued $^1$H and $^{13}$C chemical shifts of coniosetin in DMSO-$d_6$ and methanol-$d_4$ at 300 K.

| | DMSO-$d_6$ | | Methanol-$d_4$ | |
|---|---|---|---|---|
| Position | $^{13}$C δ (ppm) | $^1$H δ (ppm) | $^{13}$C δ (ppm) | $^1$H δ (ppm) |
| 8 | 35.44 | 1.72, 1.01 | 37.20 | 1.77 d, br, 1.10 m |
| 9 | 27.59 | 1.94 d, 1.00 | 29.47 | 2.01 d, br, 1.06 m |
| 10 | 39.28 | 1.57 | 41.39 | 1.66 m |
| 11 | 130.42 | 5.18 m | 132.05 | 5.19 |
| 12 | 131.96 | 5.72 t | 134.03 | 5.78 t |
| 13 | 131.31 | 5.91 t | 132.71 | 5.90 t |
| 13a | 127.83 | 5.52 m | 129.12 | 5.51 m |
| 13b | 17.73 | 1.65 d | 18.23 | 1.67 d |
| 14 | 198.23 | — | 201.30 | — |
| 14-OH | — | 17.49 s, br | — | — |
| 15 | 99.46 | — | 101.50 | — |
| 16 | 179.52 | — | 181.53 | — |
| 17 | — | 9.22 s, br | — | — |
| 18 | 66.57 | 3.62 | 68.19 | 3.62 br |
| 19 | 191.09 | — | 193.51 | — |
| 20 | 65.66 | 3.91 | 68.11 | 4.06 br |
| 20-OH | — | 4.76 d | — | — |
| 21 | 20.67 | 1.17 d | 20.65 | 1.29 d, br |

TABLE 3

$^1$H and $^{13}$C chemical shifts of coniosetin in CDCl$_3$ at 300 K.

| Position | $^{13}$C δ (ppm) | $^1$H δ (ppm) |
|---|---|---|
| 1 | 49.84 | — |
| 1-Me | 13.76 | 1.44 |
| 2 | 49.25 | 3.22 |
| 3 | 131.50 | — |
| 3-Me | 22.23 | 1.61 |
| 4 | 126.01 | 5.20 |
| 5 | 39.13 | 1.85 |
| 6 | 42.54 | 1.82, 0.90 |
| 7 | 33.54 | 1.54 |
| 7-Me | 22.46 | 0.94 |
| 8 | 35.78 | 1.79, 1.13 |
| 9 | 28.30 | 1.99, 1.08 |
| 10 | 39.73 | 1.68 |
| 11 | 130.19 | 5.23 |
| 12 | 132.62 | 5.83 |
| 13 | 131.39 | 5.89 |
| 13a | 128.19 | 5.52 |
| 13b | 18.02 | 1.70 |
| 14 | 200.23 | — |
| 14-OH | — | — |
| 15 | 100.28 | — |
| 16 | 179.33 | — |
| 17 | — | 6.19 |
| 18 | 65.43 | 3.71 |
| 19 | 190.95 | — |
| 20 | 67.80 | 4.05 |
| 20-OH | — | — |
| 21 | 19.56 | 1.34 |

EXAMPLE 8

Inhibitory Effect of Coniosetin in the Agar Diffusion Test

Agar plates were prepared with a 2 ml inoculum of *Staphylococcus aureus* in 200 ml of agar solution, a 2 ml inoculum of *Escherichia coli* in 200 ml of agar; a 2 ml inoculum of *Candida albicans* in 200 ml of agar solution; a 1 ml inoculum of *Aspergillus niger* in 200 ml of agar solution and a 3 ml inoculum of *Streptomyces murinus* in 200 ml of agar solution. The coniosetin was applied in a 10 mM solution to disks with a diameter of 6 mm and placed on the agar plate. The inoculated Staphylococcus, *E. coli* and Candida plates were incubated at 37° C. for 16 hours, the *A. niger* plate was incubated at 28° C. for 40 hours, and the Streptomyces plate was incubated at 28° C. for 16 hours. Zones of inhibition with the following diameters (mm) were then observed.

TABLE 4

| Amount of coniosetin | S. aureus | E. coli | C. albicans | A. niger | S. murinus |
|---|---|---|---|---|---|
| 10 μl | 13 | 0 | 9 | 0 | 0 |
| 20 μl | 14.5 | 0 | 10 | 0 | 9 |
| 40 μl | 15.5 | 0 | 10.5 | 8 | 10 |

What is claimed is:

1. A compound of the formula I:

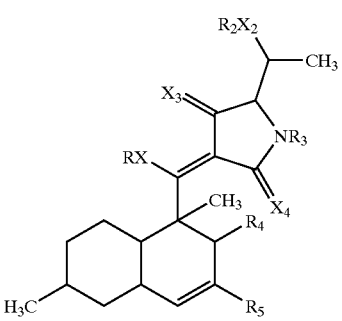

wherein:

R is:
- A. H, or
- B. C$_1$–C$_6$-alkyl, C$_2$–C$_6$-alkenyl or C$_2$–C$_6$-alkynyl, wherein alkyl, alkenyl and alkynyl are straight-chain or branched and are optionally substituted once or twice by:
  - B.1 —OH,
  - B.2 =O,
  - B.3 —O—C$_1$–C$_6$-alkyl, in which alkyl is straight-chain or branched,
  - B.4 —O—C$_2$–C$_6$-alkenyl, in which alkenyl is straight-chain or branched,
  - B.5 —aryl,
  - B.6 —NH—C$_1$–C$_6$-alkyl, in which alkyl is straight-chain or branched,
  - B.7 —NH—C$_2$–C$_6$-alkenyl, in which alkenyl is straight-chain or branched,
  - B.8 —NH$_2$ or
  - B.9 halogen,
  in which substituents B.1 to B.9 may be further substituted by —CN, amide or oxime functions, R$_2$X$_2$ is OH,
R$_3$ is H,
R$_4$ is penta-1,3-dienyl,
R$_5$ is methyl,
X, X$_3$ and X$_4$ are, independently of one another, O, NH, N—C$_1$–C$_6$-alkyl, N—C$_2$–C$_6$-alkenyl, N—C$_2$–C$_6$-alkynyl, wherein alkyl, alkenyl and alkynyl are straight-chain or branched, N-acyl, N-aryl, N—O—R or S, or a stereoisomeric form of the compound of formula I, or a physiologically tolerated salt of any of the foregoing.

2. A compound of the formula II:

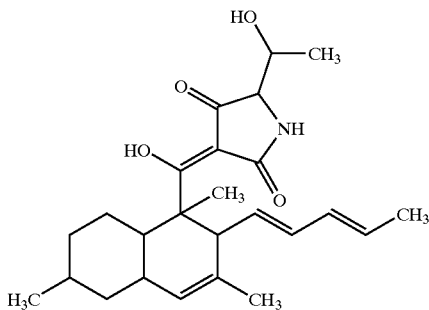

a stereoisomeric form of the compound of formula II, or a physiologically tolerated salt of any of the foregoing.

3. A compound of the formula IIIA:

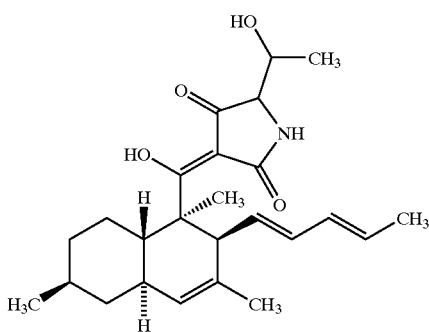

or a physiologically tolerated salt thereof.

4. A compound of the molecular formula: $C_{25}H_{35}NO_4$ (coniosetin), obtained by fermenting *Coniochaeta ellipsoidea* Udagawa (DSM 13856), one or more of its variants, one or more of its mutants, or a combination of any of the foregoing until the compound coniosetin accumulates in the culture broth, and subsequently isolating the compound, or one of the pharmacologically acceptable salts thereof.

5. A method for preparing a compound as claimed in claim 1, comprising the steps of:
   a) fermenting the microorganism *Coniochaeta ellipsoidea* Udagawa (DSM 13856), one or more of its variants, one or more of its mutants, or a combination of any of the foregoing in a culture to produce the compound,
   b) isolating the compound, and
   c) optionally converting the compound into one or more of the pharmacologically acceptable salts of the compound.

6. The method as claimed in claim 5, wherein the fermenting is carried out in a nutrient medium comprising a carbon and nitrogen source and customary inorganic salts and trace elements, under aerobic conditions.

7. The method as claimed in claim 5, wherein the fermenting is carried out in a nutrient medium comprising 0.5 to 5% malt extract and 0.5 to 5% oatmeal as carbon sources.

8. The method as claimed in claim 5, wherein the fermenting is carried out under aerobic conditions at a temperature ranging from 20 to 35° C. and at a pH ranging from 4 to 10.

9. The method as claimed in claim 6, wherein the nutrient medium comprises 0.5 to 5% malt extract and 0.5 to 5% oatmeal as carbon sources.

10. The method as claimed in claim 6, wherein the fermenting is carried out at a temperature ranging from 20 to 35° C. and at a pH ranging from 4 to 10.

11. A composition comprising at least one compound as claimed in claim 1, at least one stereoisomeric form of the compound claimed in claim 1, or a mixture of stereoisomeric forms of the at least one compound claimed in claim 1 in any ratio, wherein any of the foregoing is in free form, as a physiologically tolerated salt, or as a mixture thereof.

12. A method for treating a patient having at least one bacterial infectious disease, comprising administering an amount of a composition as claimed in claim 11, wherein the amount is effective for the treating.

13. A method for treating a patient having at least one mycosis, comprising administering to the patient an amount of a composition as claimed in claim 11, wherein the amount is effective for the treating.

14. The composition as claimed in claim 11, further comprising one or more physiologically acceptable carriers and optionally comprising one or more suitable excipients.

15. The compound of formula II as claimed in claim 2, wherein the compound has the structure:

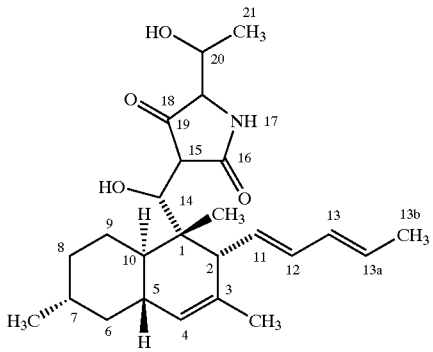

or a physiologically tolerated salt thereof.

16. A method for prophlaxis at least one bacterial infectious disease in a patient in need of such preventing, comprising administering an amount of a composition as claimed in claim 11, wherein the amount is effective for the prophylaxis.

17. A method for prophylaxis at least one mycosis in a patient in need of such preventing, comprising administering an amount of a composition as claimed in claim 11 wherein the amount is effective for the prophylaxis.

* * * * *

UNITED STATES PATENT AND TRADEMARK OFFICE
CERTIFICATE OF CORRECTION

PATENT NO. : 6,599,930 B2
DATED : July 29, 2003
INVENTOR(S) : Laszlo Vertesy et al.

It is certified that error appears in the above-identified patent and that said Letters Patent is hereby corrected as shown below:

Column 13,
Lines 38-39, "*elllpsoidea*" should read -- *ellipsoidea* --.

Column 14,
Lines 33-45,

" 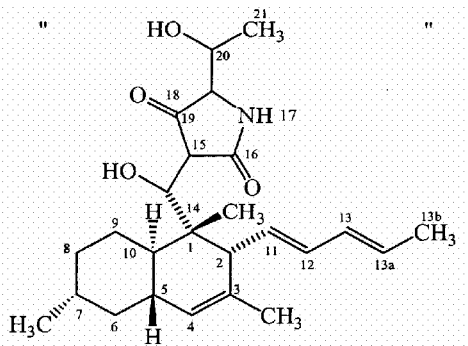 " should read 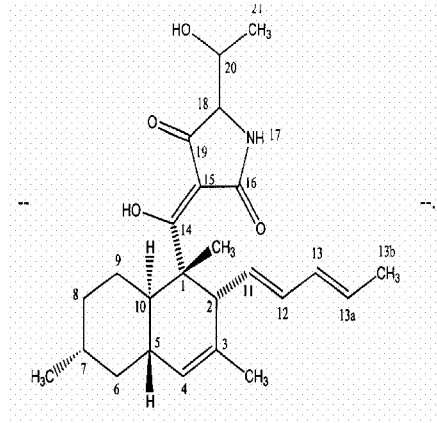 --.

Line 49, "prophlaxis at" shoud read -- prophylaxis of at --.
Lines 50 and 55, "preventing," should read -- prophylaxis, --.
Line 54, "prophylaxis at" should read -- prophylaxis of at --.
Line 56, "claim 11 wherein" should read -- claim 11, wherein --.

Signed and Sealed this

Second Day of March, 2004

JON W. DUDAS
*Acting Director of the United States Patent and Trademark Office*